United States Patent [19]

Baechler

[11] Patent Number: 5,233,727
[45] Date of Patent: Aug. 10, 1993

[54] DEVICE FOR MEASURING THE THICKNESS AND/OR UNEVENNESS OF WEBS OR WADDING ON SPINNING PREPARATION MACHINES.

[75] Inventor: Francois Baechler, Wermatswil, Switzerland

[73] Assignee: Zellweger Uster AG, Uster, Switzerland

[21] Appl. No.: 717,662

[22] Filed: Jun. 19, 1991

[30] Foreign Application Priority Data

Jul. 4, 1990 [CH] Switzerland .................. 02219/90-2

[51] Int. Cl.⁵ .................. D01G 23/06; G01L 5/04
[52] U.S. Cl. ...................... 19/300; 19/0.24; 73/159
[58] Field of Search ............... 19/300, 105, 0.23, 0.24, 19/239, 277, 279, 280, 281, 266, 161.1; 73/159

[56] References Cited

U.S. PATENT DOCUMENTS

| | | | |
|---|---|---|---|
| 4,414,710 | 11/1983 | Bolen | 19/105 |
| 4,506,413 | 3/1985 | Leifeld | 19/300 |
| 4,520,531 | 6/1985 | Hergeth | 19/105 |
| 4,817,247 | 4/1989 | Leifeld et al. | 19/105 |
| 4,939,815 | 7/1990 | Leifeld | 19/105 |

FOREIGN PATENT DOCUMENTS

| | | | |
|---|---|---|---|
| 3141537 | 5/1983 | Fed. Rep. of Germany | 19/300 |
| 3810575 | 10/1989 | Fed. Rep. of Germany | |
| 2322943 | 5/1977 | France | 19/239 |
| 641637 | 6/1962 | Italy | 19/239 |
| 986979 | 1/1983 | U.S.S.R. | 19/105 |
| 956146 | 4/1964 | United Kingdom | |

Primary Examiner—Clifford D. Crowder
Assistant Examiner—Michael A. Neas
Attorney, Agent, or Firm—Burns, Doane, Swecker & Mathis

[57] ABSTRACT

In a textile fiber preparation machine, thickness and/or unevenness characteristics of a lap (W) formed by a web or wadding of textile fibers being fed in the machine are determined for individual longitudinal strips spaced across the width of the lap. A plurality of individual sensors (2) are arranged next to one another over the width of the lap (W) and press the lap (W) against a stationary guide (4,5, 6—6'). Each of the sensors (2) is movable toward and away from the guide and is resiliently biased toward the guide. The amount of movement of an individual sensor (2) away from the guide by the lap is a measure of the thickness of the lap portion being contacted by that sensor. The use of individual sensors arranged end to end across the width of the lap improves sensitivity so that even brief changes in thickness when the lap has a high transport speed can be measured reliably. Furthermore, the apparatus can be adapted quickly and simply to changing lap widths.

16 Claims, 3 Drawing Sheets

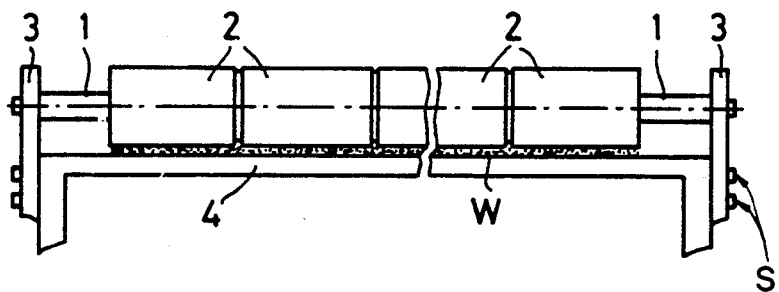
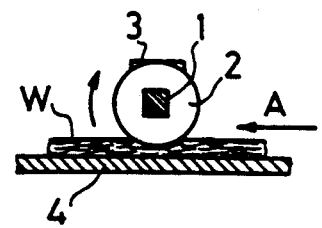
FIG. 1    FIG. 1A
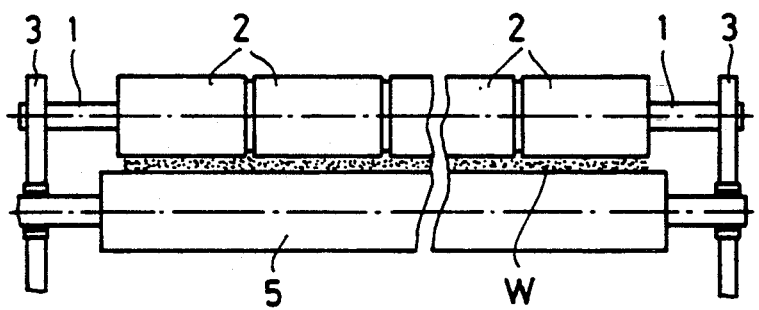
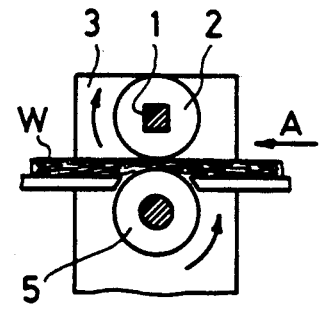
FIG. 2    FIG. 2A
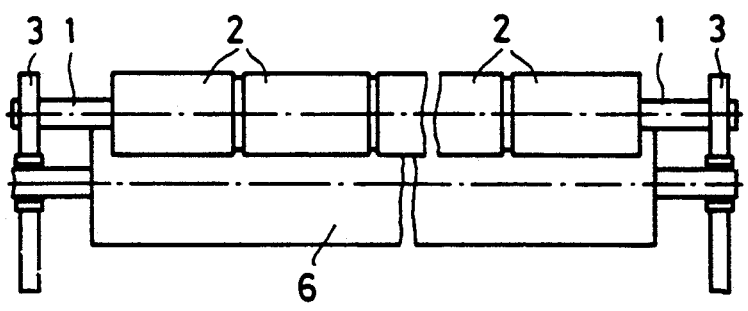
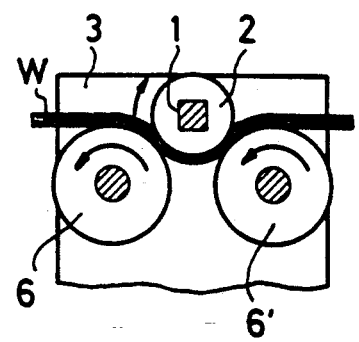
FIG. 3    FIG. 3A

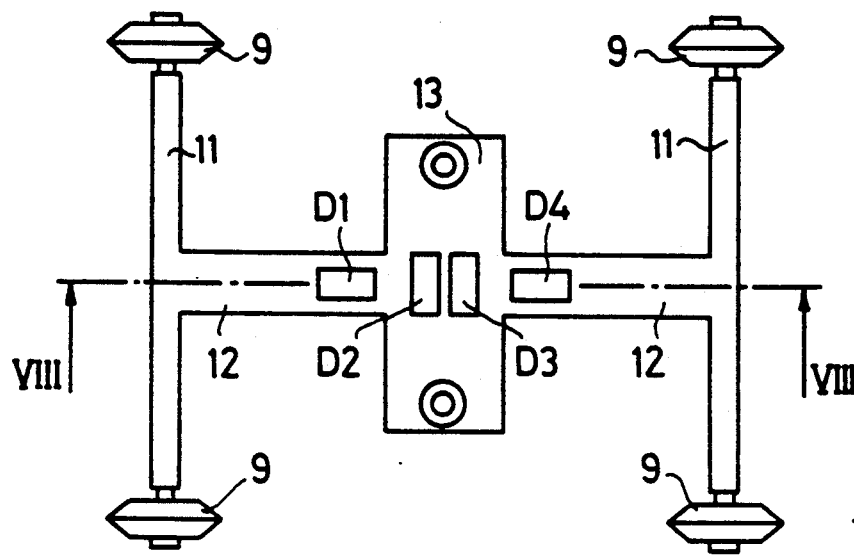
FIG. 7
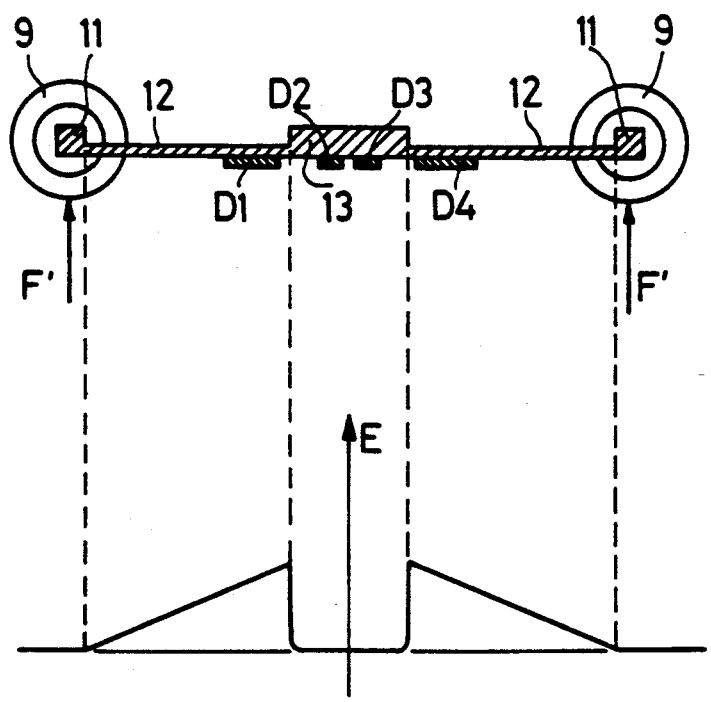
FIG. 8
FIG. 9

DEVICE FOR MEASURING THE THICKNESS AND/OR UNEVENNESS OF WEBS OR WADDING ON SPINNING PREPARATION MACHINES.

FIELD OF THE INVENTION

The present invention relates to apparatus for handling web-like assemblies of textile fibers in the course of preparing the fibers for spinning and is concerned particularly with measuring the thickness and/or unevenness of such web-like assemblies during their handling in the apparatus.

BACKGROUND

In the fiber preparation field, webs or waddings of textile fibers (e.g. cotton fibers) of substantial width may constitute the feed material for certain of the fiber treating machines (e.g. carding machines). Such web-like bodies, referred to herein as laps, are generally continuous in length and they are fed on a generally continuous basis to the treating machines. In at least some such operations, it is desirable to ascertain thickness information concerning the laps as they are being fed. One manner of obtaining lap thickness information is to pass the lap through a gap between guide means and a movable sensor that is biased toward the guide means. As the thickness of the lap varies, the position of the sensor relative to the guide means varies and this provides a measure of the thickness and/or unevenness of the lap.

In known devices of this type, a single measuring roller extends over the entire maximum lap width and the position of this single measuring roller relative to a guide roller is taken as an indication of lap thickness. However, the travel of this measuring roller can only represent the highest particular lap thickness value that occurs locally at any zone across the entire length of the measuring roller. Moreover, a measuring roller of a length sufficient to extend across the entire lap width necessarily has a relatively high inertia, and systems utilizing such long measuring rollers are also inflexible because they cannot be matched to different lap widths.

SUMMARY OF THE INVENTION

According to the present invention, the sensing of lap thickness is accomplished by sensor means formed by a plurality of individual sensors arranged next to one another over the width of the lap, with the individual sensors being individually movable by different widthwise zones of the lap being advanced through a measuring gap formed by the sensor means and a guide on the opposite side of the lap.

Since the individual sensors have only a fraction of the mass moment of inertia of the long measuring rollers known heretofore, the measuring device becomes correspondingly more sensitive, and this means that brief variations in the lap thickness can be measured even on high speed machines. The measurement result of each individual sensor represents a corresponding strip-shaped region of the lap, so that the measurement results of all the individual sensors reproduce the thickness distribution over the lap width. Finally, the construction of the system from individual sensors allows the measuring device to be adapted to changing lap widths in a simple way.

BRIEF DESCRIPTION OF THE DRAWINGS

Exemplary embodiments of the invention are explained in more detail below with reference to the accompanying drawings in which FIG. 1 is a front view of an exemplary embodiment of a device according to the invention;

FIG. 1a is a side sectional view of the device of FIG. 1;

FIG. 2 is a front view of another exemplary embodiment of a device in accordance with the invention;

FIG. 2a is a side sectional view of the device of FIG. 2;

FIG. 3 is a front view of another exemplary embodiment of a device in accordance with the invention;

FIG. 3a is a side sectional view of the device of FIG. 3;

FIG. 7 shows a view in the direction of the arrow VII of FIG. 5;

FIG. 8 shows a view in the direction of the arrow VIII of FIG. 7; and

FIGS. 9 and 10 show diagrams to explain the mode of operation.

DETAILED DESCRIPTION OF PREFERRED EMBODIMENTS

Figure 4:
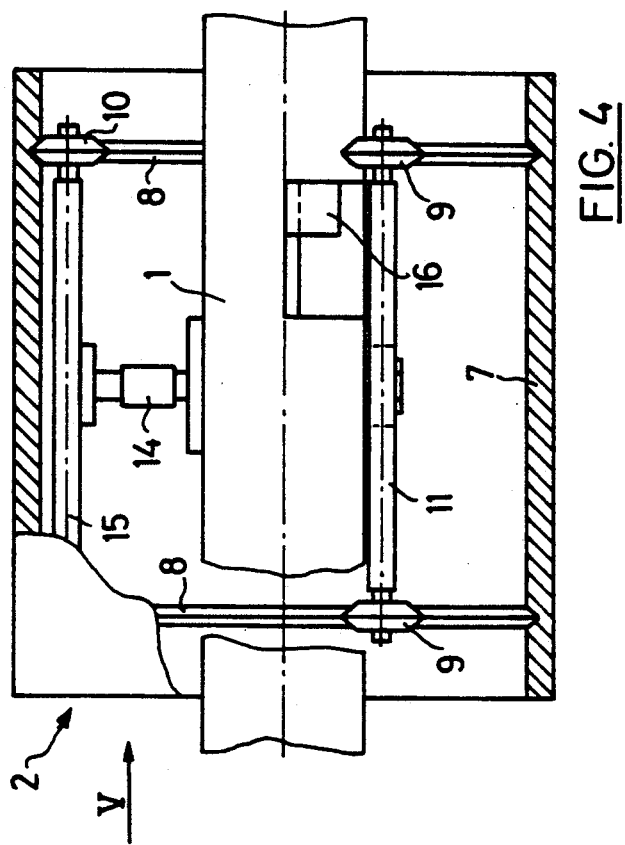
FIG. 4 is an axial section view through the measuring roller in FIG. 1.

The principle by which the thickness or unevenness of laps (fibrous webs or waddings being fed lengthwise in such spinning preparation machines as cards, draw frames, combing machines and the like) is measured will be evident from FIGS. 1 to 3. This measurement is made by measuring the distance between guide means for the lap W and thickness sensing means which presses the lap against the guide means. The guide means may be visualized as being fixed or stationary in space even though its lap-contacting surface may be cylindrical and may rotate. In the present invention, the sensing means is formed as illustrated by a plurality of measuring rollers 2 mounted on a common shaft 1.

The shaft 1, preferably formed by a beam, is mounted in a holder 3 adjustable relative to the guide means for the lap W. The shaft 1 may have a rectangular cross-section for example. The holder 3 is formed by suitable supporting arms, bearing blocks or the like. The pressure force of the measuring rollers 2 on the lap W is determined by setting the distance between the shaft 1 and the guide or by means of the holder 3 by adjusting the holder via screws.

The exemplary embodiments illustrated in FIGS. 1 to 3 differ from one another in the design of the guide means for the lap W. The guide means is formed in FIG. 1 by a plane plate 4. In FIG. 2, the guide means is a single roller 5 rotating about a stationary axis, and in FIG. 3 the guide means is shown as a pair of rollers 6 and 6', each rotating about a fixed axis. The arrangement of FIG. 2 normally is preferred, because of its simplicity and a lack of friction between the lap and the lap-containing surface of the guide means.

The direction of transport of the lap W is designated in each case by an arrow A, and the guide roller 5 and at least one of the guide rollers 6 and 6' are driven so that the lap contacting surfaces thereof move in the direction of movement of the lap. The measuring rollers 2 are freely rotatable on the common shaft 1.

The essential feature common to all the exemplary embodiments is the plurality of measuring rollers 2 which are arranged on the beam-shaped shaft 1 and which each act on their own and independently of the others as sensors for the thickness of the associated strip-shaped region of the lap W. Because the mass moment of inertia of each of the short measuring rollers 2 is low in comparison with that of a single measuring roller extending over the entire machine width, the individual measuring rollers 2 can also measure brief variations in the thickness of the lap W on high speed machines. The modular construction of the thickness sensor from the individual measuring rollers 2 allows the measuring system to be matched to different lap widths in a simple way, and the range adaptation of the measuring system is likewise possible in a simple way by adjusting the distance between the shaft 1 and the guide means (4, 5, and 6, 6'). As will be evident from FIGS. 4 to 6, moreover, the entire measuring system is free of any lever arm and of play.

As illustrated, the measuring rollers 2 are formed by hollow cylinders 7 possessing, on their inner faces, two parallel spaced grooves 8 which extend transversely relative to the cylinder axis and in each of which three rolls 9, 9 and 10 of a triaxial suspension are guided. The suspension includes two axles 11 carried by the end portions of a web 12 the thickened central or "bridge" portion 13 of which is fastened to the underside of the shaft 1. A roll 9 is rotatable on each end of each end of the axles 11 and engages in a groove 8 in the hollow cylindrical measuring roll body 7. The side parts of the strip-shaped web 12 beyond the bridge 13 are resilient. Hence, the web 12 acts as a measuring spring. The carriage-like roll carrier 11-12 is thus mounted resiliently on the shaft 1.

The suspension also includes a centering axle 15 carrying two guide rolls 10 which engage the grooves 8. This axle 15 is fastened to the top side of the beam-shaped shaft 1 via a connecting piece 14 which is designed in the manner of an adjustable prop. It is an assembly in which the upper end and lower end parts are resiliently urged apart, with the lower part being connected to the shaft 1 and the upper part carrying the centering axle 15. When the thickness of a lap contacted by the cylinder 7 shifts the cylinder upwardly, the axles 11 carrying the tracer rolls 9 also shift upwardly and the centering axle 15 is correspondingly adjusted in the same direction, so that all of the rolls 9 and 10 are constantly guided in the grooves 8.

The triaxial suspension described therefore constitutes a resilient connection between the shaft 1 and the hollow cylinder 7 which allows a vertical adjusting movement of the hollow cylinder 7 and consequently of each measuring roller 2 in relation to the stationary shaft 1. This adjusting movement, the upward extent of which is limited by stops 16, brings about a corresponding bending of the measuring spring 12. As can be understood from FIGS. 4 to 6, the stops 16 are located in the path of movement of the axles 11 and therefore act on these.

Figure 5:
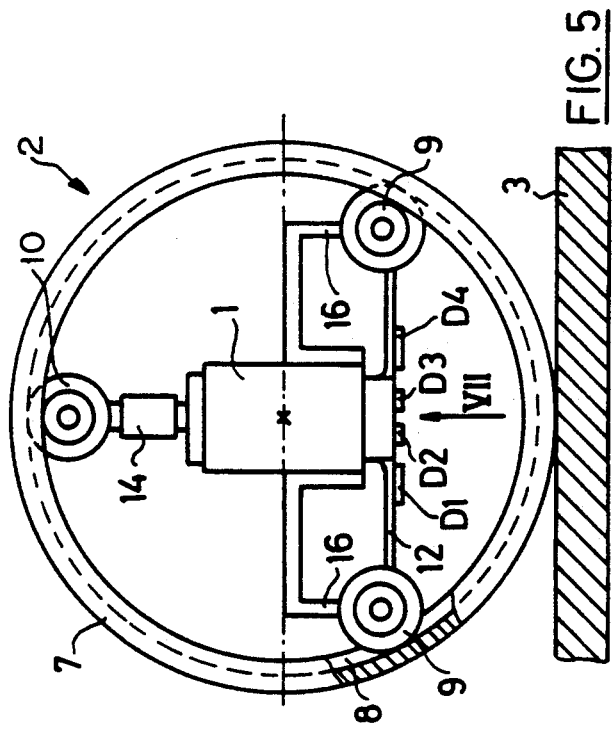
FIGS. 5 and 6 are similar in that each is taken in the direction of the arrow V is FIG. 4, but they show the conditions that exist in two different positions of the measuring roller surface relative to the opposing guide.
Figure 6:
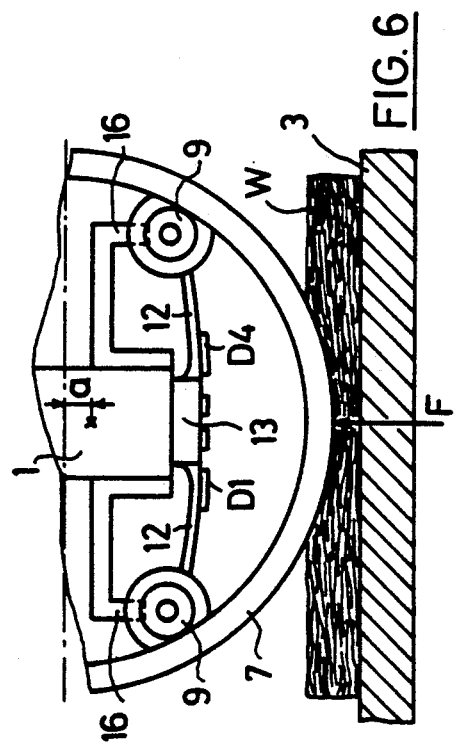

In the operating state shown in FIG. 5, the measuring roller 2 is in the state of rest and, for example, bears against the guide plate 4, the connecting piece 14 being set in such a way that the measuring spring 12 is not deformed. Now as soon as a lap W enters between the guide plate 4 and measuring roller 2, the measuring roller 2 is pressed upwards with a force F in dependence on the instantaneous local thickness of the lap W, this bringing about a corresponding bending of the measuring spring 12. This operating state is illustrated in FIG. 6, where it can be seen that the axis of the hollow cylinder 7 has been displaced upwards from the mid-axis of the shaft 1 by the amount of adjustment travel a. As a result of the bending of the measuring spring 12, strains occur in its material, and these can be converted into electrical quantities by strain gauges suitably arranged on the measuring spring 12 and can thereby be measured. The strain gauges are adhesively bonded or sputtered onto the measuring spring 12.

As can be understood from consideration especially of FIGS. 7 and 8, two strain gauges D2 and D3 are arranged on the measuring spring 12 in the region of the bridge 13 transversely relative to the longitudinal direction of the measuring spring 12, and a strain gauge D1 and D4 is arranged immediately adjacent to the bridge 13 on each side in the longitudinal direction of the measuring spring 12. In FIG. 9, the trend of the strain E, which is a function of the force F' acting on the tracer rolls 9, is plotted against the length of the measuring spring 12. It can be seen from this diagram that the strain in the region of the strain gauges D2 and D3 is equal to zero and in the region of the strain gauges D1 and D4 is at a maximum. Accordingly, the differential values of the pairs of strain gauges D1, D2 and D3, D4 are used for measuring the strain.

Figure 10:
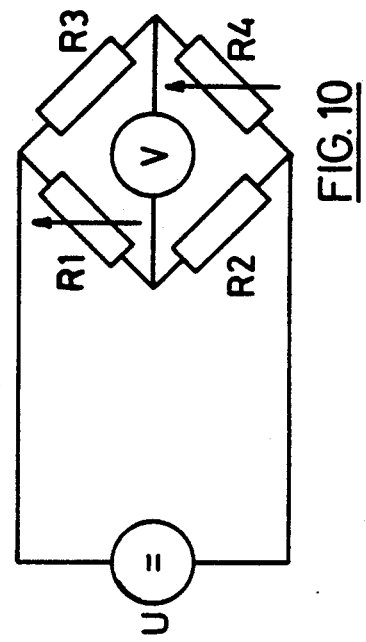

As is known, each strain gauge D1 to D4 has a specific electrical resistance R1 to R4, these resistances all being equal. Since the relative change of resistance during the bending of the measuring spring 12 is proportional to the strain of the strain gauges, the strain can be determined by measuring this change of resistance. According to FIG. 10, this is carried out by means of a Wheatstone bridge connection consisting of four branches which are formed by the resistors R1 to R4 connected annularly together. When a supply voltage U is applied to the junction points between the resistors R1 and R3 on the one hand and R2 and R4 on the other hand, it is possible to tap at the two remaining junction points an output voltage V which is proportional to the bridge detuning and which is itself proportional to the sum of the strains of the individual strain gauges D1 to D4. But since the strain E is a function of the force F' acting on the tracer rolls 9 and this is itself a function of the force F acting on the measuring roller 2, the output voltage V is a measure of the force F and therefore of the thickness of the lap W.

The output voltage V is measured on each of the measuring rollers 2 arranged end to end in succession over the width of the lap, for which purpose corresponding electrical leads in the beam-shaped shaft 1 are guided outwards from each measuring roller 2 to an evaluation station arranged on one side of the machine. The shaft 1 with the measuring rollers 2 thereon extends over the entire machine width. If the particular lap W is narrower than this, only the measuring rollers 2 bearing against the lap are operative and signals from the inactive measuring rollers are not picked up. Each of the active measuring rollers 2 measures the trend of the thickness of the associated strip of the lap W over its length, and a comparison of the measurement results of the individual measuring rollers 2 at a specific time provides a thickness profile over the width of the lap W. Since the measuring rollers 2 at all events press from above onto the lap W with a definite adjustable pressure, they act at the same time as compacting members which compact the lap. Of course, this compacting pressure is set equal for all the measuring rollers 2. Range adaptations of the measuring system, that is to say adaptations to the thickness of the lap W to be processed, are possible in a simple way by an appropriate adjustment on the holder 3 (FIG. 1). The measuring system is therefore extremely flexible and can be adapted simply to different lap widths and lap thicknesses.

What is claimed is:

1. In a machine for preparing textile fibers for spinning and in which a web of substantial width is moved along a path, apparatus for measuring thickness characteristics of said moving web comprising guide means over which said web moves, and measuring means on the side of said web opposite said guide means, said measuring means including a plurality of web contacting elements in the form of hollow measuring rollers arranged end to end across the width of said web and being independently rotatable about their central axes, and being independently movable relative to said guide means so that each measuring roller moves to a location determined by the thickness of the web portion passing between said guide means and that particular measuring roller, there being provided a common shaft extending through all of such hollow measuring rollers, and wherein an individual resilient suspension is provided for each of said measuring rollers to individually suspend its measuring roller from said shaft for said independent rotation and said independent movement relative to said guide means.

2. Apparatus according to claim 1, including stain gauge means associated with each of said suspensions for providing signals in response to changes in the positions of individual ones of said measuring rollers.

3. Apparatus according to claim 1, wherein said measuring means includes a sensor mounted within each of said measuring rollers for sensing the movement of such measuring roller relative to said guide means.

4. Device for measuring the thickness and/or unevenness of webs or waddings, referred to hereafter as laps, on spinning preparation machines, with a guide for the lap and with a thickness sensor which presses the lap against the guide and is adjustable relative to the latter and the adjustment of which is a measure of the thickness and/or unevenness of the lap, characterized in that the thickness sensor is formed by a plurality of individual measuring rollers arranged next to one another over the width of the lap, and a common shaft extending through all of the measuring rollers, the measuring rollers being independently suspended from the shaft for independent rotation and independent adjustment by the lap.

5. Device according to claim 4, wherein the measuring rollers are formed by hollow cylinders and are connected to the common shaft by a resilient suspension.

6. Device according to claim 5, wherein the resilient suspension has at least three pairs of rolls which are arranged on axles oriented parallel to the longitudinal axis of the common shaft and which, on the one hand, are mounted resiliently on the common shaft and which, on the other hand, carry the hollow cylinders on their inner wall.

7. Device according to claim 6, wherein the rolls are guided in corresponding grooves on the inner wall of the hollow cylinders.

8. Device according to claim 7, wherein two of the axles carrying pairs of rolls are carried by a support which resembles a leaf spring and which is arranged perpendicularly to the axis of the common shaft and perpendicularly to the direction of adjustment of the hollow cylinders.

9. Device according to claim 8, wherein the support resembling a leaf spring is designed as a measuring spring and is equipped with at least one pair of strain gauges, one strain gauge being arranged in a region of maximum strain of the measuring spring brought about by the adjustment of the hollow cylinder, and the other strain gauge being arranged in a region of minimum strain of the measuring spring.

10. Device according to claim 9, wherein the common shaft has a rectangular cross-section with two side faces parallel to the direction of adjustment of the hollow cylinders, and wherein the measuring spring is fastened to the bottom face of the common shaft adjacent to the guide.

11. Device according to claim 10, wherein the measuring spring in its middle part has a bridge-shaped thickening and in the region of this thickening is fastened to the common shaft, and wherein the strain gauges arranged in a region of minimum strain of the measuring spring are provided in the region of this thickening.

12. Device according to claim 11, characterized by stops for limiting the bending of the measuring spring.

13. Device according to claim 4 including a holder to which the common shaft is mounted, the common shaft being of non-circular cross section and mounted in a non-circular recess in the holder so as to be fixed against rotation about its longitudinal axis, means for adjusting the holder such that the distance between the longitudinal axis of the shaft and the guide can be changed.

14. Device according to claim 4, wherein the guide is plate-shaped.

15. Device according to claim 4, wherein the guide is roller-shaped.

16. In a machine for preparing textile fibers for spinning and in which a web of substantial width is moved along a path, apparatus for measuring thickness characteristics of said moving web comprising guide means over which said web moves, and measuring means on the side of said web opposite said guide means, said measuring means including a plurality of web contacting elements in the form of hollow measuring rollers arranged end to end across the width of said web and being independently rotatable about their central axes, and being independently movable relative to said guide means so that each measuring roller moves to a location determined by the thickness of the web portion passing between said guide means and that particular measuring roller, said measuring means including a sensor mounted within each of said measuring rollers for sensing the movement of such measuring roller relative to said guide means.

* * * * *